United States Patent [19]

Naruse et al.

[11] Patent Number: 4,474,064
[45] Date of Patent: Oct. 2, 1984

[54] ULTRASONIC FLAW DETECTOR

[75] Inventors: Akisuke Naruse; Tatsukuma Hosono; Kazuo Takaku; Shigeru Kajiyama, all of Hitachi, Japan

[73] Assignees: Hitachi, Ltd., Tokyo; Hitachi Engineering Co., Ltd., Ibaraki, both of Japan

[21] Appl. No.: 355,357

[22] Filed: Mar. 8, 1982

[30] Foreign Application Priority Data

Mar. 10, 1981 [JP] Japan ................................ 56-34791

[51] Int. Cl.³ ...................... G01N 29/04; G21C 17/00
[52] U.S. Cl. ........................................ 73/622; 73/640; 376/249; 376/252
[58] Field of Search ................... 73/622, 633, 640; 376/249, 252

[56] References Cited

U.S. PATENT DOCUMENTS

| | | | |
|---|---|---|---|
| 3,765,229 | 10/1973 | Spencer et al. | 73/640 |
| 3,863,496 | 2/1975 | Hiramatsu et al. | 73/640 |
| 3,934,457 | 1/1976 | Clark et al. | 376/249 |
| 4,117,733 | 10/1978 | Gugel | 376/249 |
| 4,131,018 | 12/1978 | Muller et al. | 376/249 |
| 4,169,758 | 10/1979 | Blackstone et al. | 376/249 |
| 4,368,644 | 1/1983 | Wentzell | 73/622 |

OTHER PUBLICATIONS

"Mechanized Equipment for In-Service Inspection of Nuclear Reactors", Lautzenheiser, *Conference on Periodic Inspection of Pressure Vessels,* London, England, May 1972, pp. 205-220.

Primary Examiner—Howard A. Birmiel
Attorney, Agent, or Firm—Beall Law Offices

[57] ABSTRACT

An ultrasonic flaw detector for detecting any flaw existing in the inner peripheral corner section of the joint portion between the barrel of a nuclear reactor pressure vessel and each of a plurality of cylindrical nozzles projecting from the barrel, by means of an ultrasonic wave applied from the outer peripheral corner section of the joint portion. The flaw detector has a probe pivotable around an axis which is made to follow up the locus of the center of curvature in the rounded surface of the outer peripheral corner section during the movement of the probe around the nozzle. According to this arrangement, it is possible to achieve a full automatic and remote control of the flaw detector except the attaching and detaching of the same, and to facilitate the processing of the signals representing the result of the flaw detection.

15 Claims, 8 Drawing Figures

ULTRASONIC FLAW DETECTOR

BACKGROUND OF THE INVENTION

The present invention relates to an ultrasonic flaw detector for detecting flaws which may exist in the inner peripheral corner of a joint portion between the barrel of a nuclear reactor pressure vessel and a nozzle projecting from the barrel. More particularly, the invention is concerned with an ultrasonic flaw detector suitable for detecting any flaw in the inner peripheral corner of the joint portion between the cylindrical nozzle and the barrel, which has an acutely rounded outer peripheral surface of a constant radius over the entire circumference of the outer peripheral corner.

In detecting flaws which may exist in the inner peripheral corner of a joint portion between a cylindrical nozzle and the barrel portion of the pressure vessel of a nuclear reactor by means of an ultrasonic wave, according to the conventional flaw detecting method, the flaw detector is manually operated by inspectors or, alternatively, the flaw detector is mechanically guided under the supervision of at least one inspector. More specifically, according to the first-mentioned method, two inspectors are engaged in the detection under the possible influence of radioactive rays: namely one inspector who manipulates the flaw detector and one inspector who records the inspection results. In the second-mentioned method, at least one inspector has to stay in the area under the possible influence of radioactive rays for continuously supervising the operation of the flaw detector. Usually, the pressure vessel of a nuclear reactor has thirty to forty cylindrical nozzles, all of which are located in a hot area or a high activity area. It is, therefore, essential to pay specific attention to prevent excessive exposure of the inspectors to radioactive rays. In consequence, such flaw detection work in the hot area is not allowed to continue over a long time.

In addition, a visible check through the naked eyes of the inspector is essential for precisely determining amount by movement of the probe of the flaw detector. Furthermore, the direction of flaw detection by ultrasonic waves transmitted from the probe varies in complicated ways in accordance with the movement of the probe, so that the processing of the detection signal is impractically complicated.

SUMMARY OF THE INVENTION

Accordingly, an object of the invention is to provide an ultrasonic flaw detector in which all kinds of operations except for the attaching and the detaching of the flaw detector, are made remotely and automatically to reduce the exposure and to improve the accuracy of flaw detection, while simplifying the processing of the detection signal, and thereby overcome the above-described problems of the prior art.

To this end, according to the invention, there is provided an ultrasonic flaw detector adapted to detect any flaw existing in the inner peripheral corner of a nozzle projecting from the barrel of the pressure vessel of a nuclear reactor by means of a probe from the outer peripheral corner of said nozzle, wherein the detector comprises means for permitting the probe to pivot about an axis on a driving unit and a probe position controlling means adapted to control the position of the probe such that the pivot axis of the probe moves following the locus of the center of curvature in an arcuately rounded surface of the outer peripheral corner section of the nozzle.

DETAILED DESCRIPTION OF THE PREFERRED EMBODIMENTS

Figure 1:
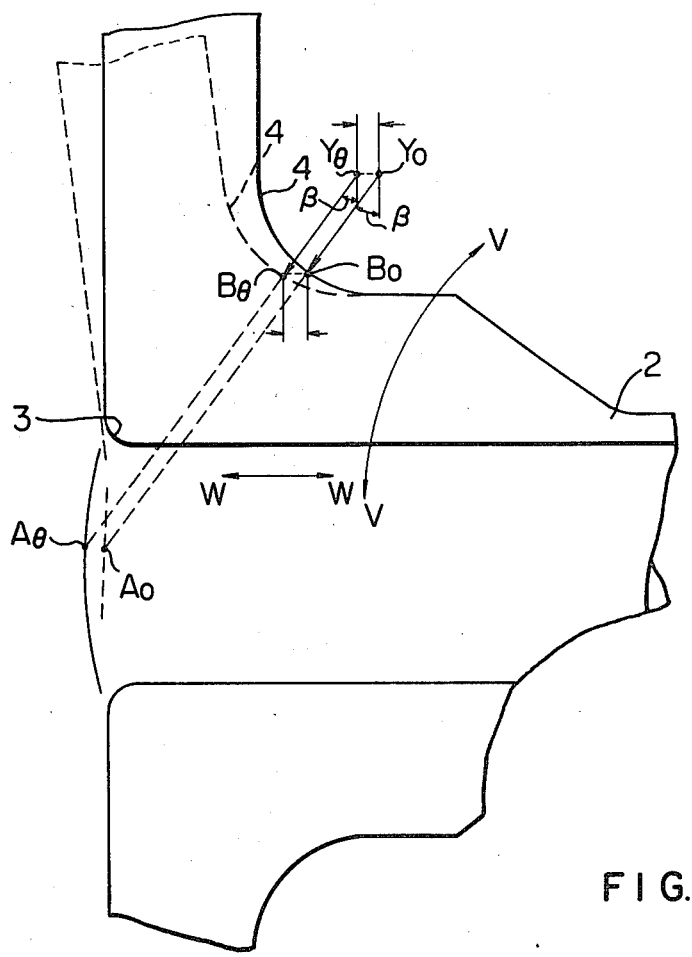
FIGS. 1 through 3 are illustrations of the principle of operation of an ultrasonic flaw detector in accordance with the present invention.
Figure 2:
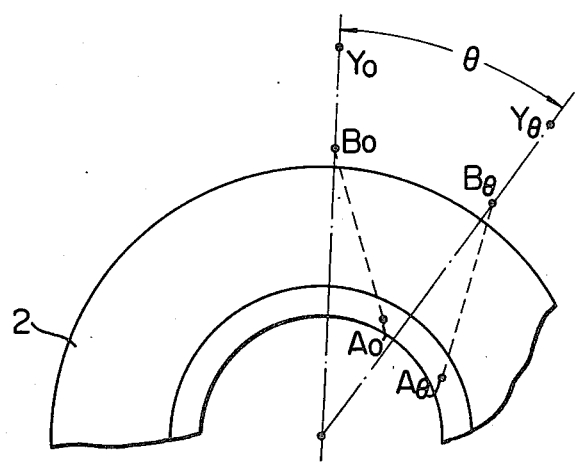
Figure 3:
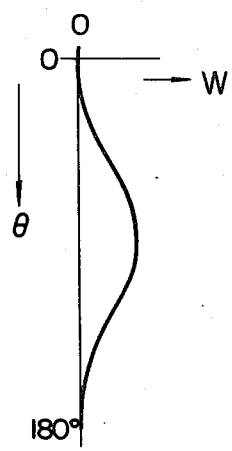

The principle of the flaw detection in accordance with the invention will be explained hereinafter with specific reference to FIGS. 1 through 3. As clearly shown in FIGS. 1 and 2, a reference symbol Y denotes the center of curvature of an outer peripheral corner section 4 (referred to as an "R-section", hereinafter) in a flanged joint portion of a cylindrical nozzle body, while a reference symbol $\beta$ denotes a directional angle of a probe directed to an inner peripheral corner section 3 (referred to as "r-section", hereinafter) with reference to a vertical line; B denotes a position of the probe on the R-section 4 of the cylindrical nozzle body 2; and A denotes a reflecting point on the r-section 3 of and the nozzle body 2 at which the main beam of ultrasonic wave is reflected.

The reference numerals having suffix 0 concern and refer to the vertical position, while those having suffix $\theta$ concern and refer to an angular position rotated from the vertical line in the direction of V. Rotation of the probe from the vertical position or 0° deg. to $\theta$° deg. in the direction of V has to be accompanied with a predetermined movement, over a distance ($B_\theta - B_0$), of the probe in the direction of W in order to detect flaws on the identical periphery of the r-section.

This amount of movement ($B_\theta - B_0$) corresponds to the amount of movement ($Y_\theta - Y_0$) of the center Y of the R-section 4 in the direction W. Namely, when the probe is rotated by an angle $\theta$, the amount of movement ($B_\theta - B_0$) of the probe in the direction W and the amount of movement ($Y_\theta - Y_0$) of the center Y of the R-section 4 are defined solely by the rotation angle $\theta$ and always take equal value to each other. These two amounts of movement are continuously changed as the rotation angle $\theta$ is changed cyclically between $\theta$ and 180° C. It is rather easy, by using known techniques such as hydraulic or electric profile control, numerical control or the like, to make the probe move following up a curve shown in FIG. 3. The basic principle of the present invention is to make the path of movement of the probe coincide with the path of movement of the center Y of the R-section. By so doing, it is possible to detect any flaw in the r-section by the probe which is moved along the R-section, easily and at a high degree of accuracy.

Figure 4:
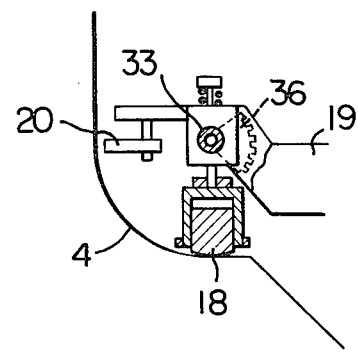
FIG. 4 is a partly-sectioned side elevational view of an ultrasonic flaw detector in accordance with the present invention.
Figure 5:
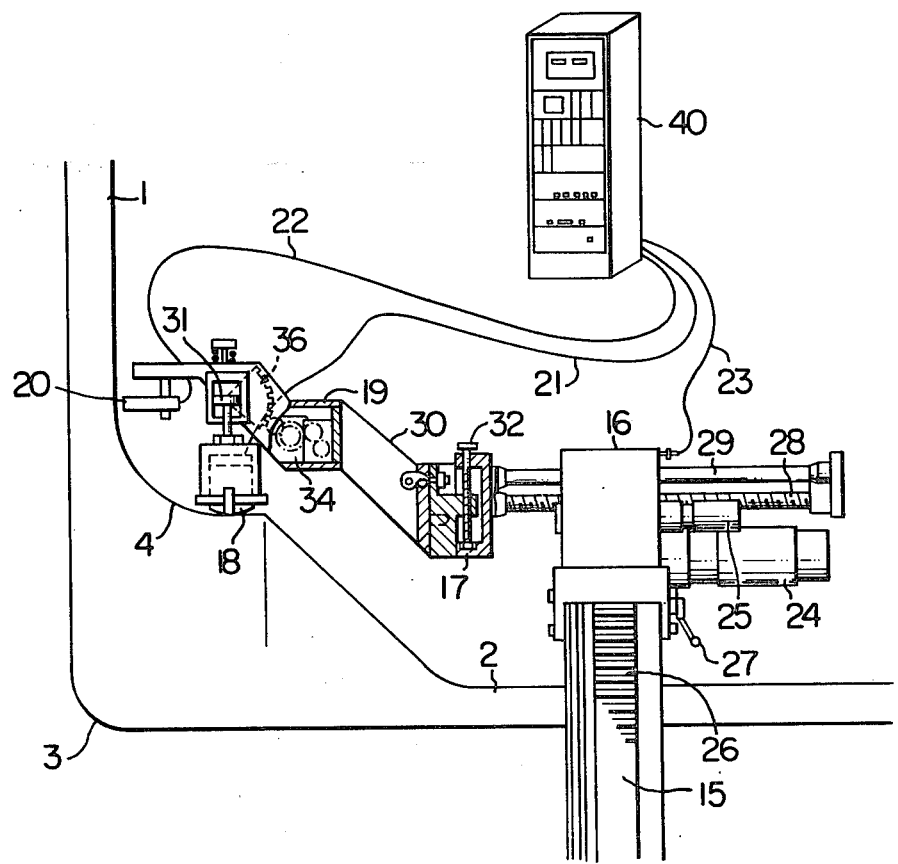
FIGS. 5 and 6 are partly-sectioned side elevational view of an ultrasonic flaw detector in the states in which the direction of flaw detection by the probe is vertical and inclined, respectively.

The construction or arrangement of the whole part of an ultrasonic flaw detector in accordance with an embodiment of the invention will be explained hereinunder with reference to FIGS. 4 and 5. The flaw detector has a detection unit adapted to be set on the nozzle body 2 for detecting flaws in the joint portion between the nozzle body 2 and the barrel 1 of a pressure vessel, and a control unit 40 for controlling the detection unit and placed in a remote control room. Furthermore, the detection unit includes a track 15 provided around the nozzle body 2 and a driving unit adapted to run along the track 15. The driving unit is constituted by a driving mechanism 16, a height adjusting mechanism 17, a probe 18, a probe rotating mechanism 19, a barrel position detecting section 20, a probe cable 21, a barrel position detecting cable 22 and a control cable 23.

A circumferential driving motor 24 and an axial driving motor 25 are incorporated by the driving mechanism 16. A pinion (not shown) driven by the circumferential driving motor 24 meshes with a rack 26 on the track 15 so that the driving unit runs in the circumferential direction of the nozzle body 2. The driving mechanism 16 is mounted on the track 15 by the manipulation of a handle 27. As the axial driving motor 25 operates, the probe 18 can be moved straight in the axial direction through the action of the feed screw 28, the guide rod 29, the height adjusting mechanism 17, the frame 30, the probe rotating mechanism 19 and a pneumatic cylinder 31. The height adjusting mechanism 17 sets the probe 18 at a predetermined level by a handle 32. The axial driving motor 25 is adapted to be driven such that the position detecting section 20 provides an output of a constant level, thereby to maintain the probe 18 at a predetermined position. Thanks to the operation of the pneumatic cylinder 31, a constant contact pressure is maintained between the probe 18 and the outer peripheral surface to ensure a stable running of the probe.

The probe 18 is supported pivotally by a shaft on the driving body. The construction for pivotally mounting the probe will be explained hereinunder with specific reference to FIGS. 5 thru 7. A pivot shaft 33 constituting the pivot axis of the probe 18 is provided on the upper end of the probe 18. The probe 18 and the pneumatic cylinder 31 in one united body pivot around the axis presented by the pivot shaft 33. The center of the pivot shaft 33 coincides with the center of the arcuate surface of the R-section 4. The probe rotating mechanism 19 incorporates a motor 34 by means of which the probe pivot shaft 33 is driven through the action of a rotation transmitting gear 35 and a segment gear 36.

Figure 6:
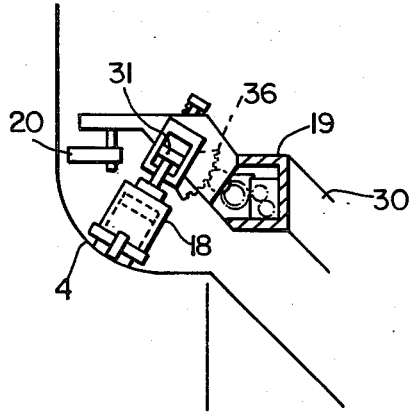

Different nozzles to be inspected to detect the flaw detection objects have different sizes of the R-section. In order to set the pivot shaft 33 of the probe 18 at the center of curvature in the rounded surface of the R-section 4 of each nozzle, the handle 32 shown in FIG. 5 is rotated to move the frame 30 supporting the probe 18 up and down and, at the same time, the stroke of the pneumatic cylinder 31 is adjusted. FIG. 5 shows how the probe pivot shaft 33 is positioned on the circle of the center of curvature in a rounded surface of the R-section 4 while the direction of flaw direction by the probe 18 is represented by $\theta = 0°$. For effecting the flaw detection, the probe 18 is pivoted around the axis of the rotary shaft 33 as shown in FIG. 6 from the position shown in FIG. 5, and is driven to move around the nozzle body 2 along the circle of center of curvature in the rounded surface of the R-section 4 over the entire periphery of the latter while making the flaw dectection.

Figure 7:
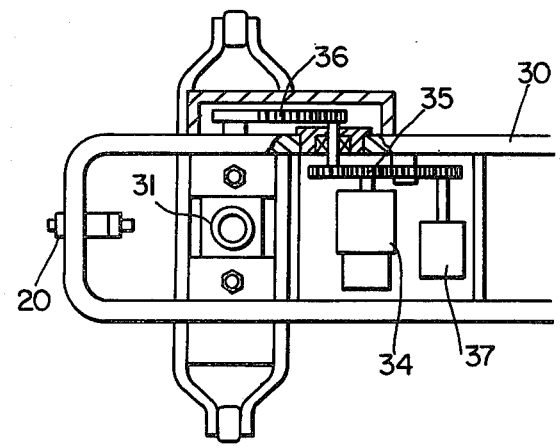
FIG. 7 is a detailed illustration of the portion of a flaw detector around the probe.
Figure 8:
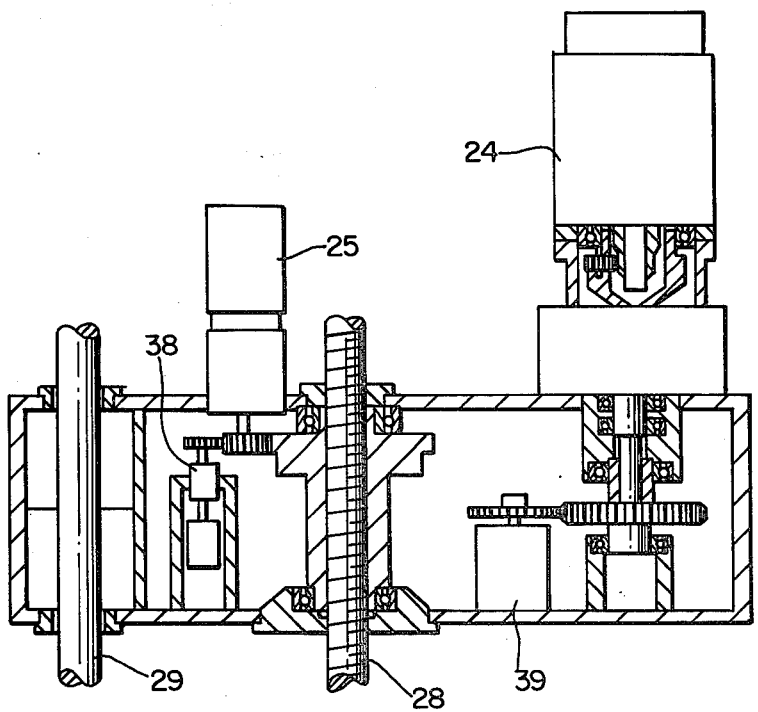
FIG. 8 is a detailed illustration of the portion of the flaw detector around a driving mechanism.

The position of flaw detection by the probe is closely related to the accuracy or precision of the ultrasonic flaw detection. According to the invention, a degree of precision of flaw detection is enhanced by moving the axis of the pivot shaft 33 following the locus of the center of curvature in a rounded surface of the R-section 4. In order to maintain the coincidence between the center of the pivot shaft and the center of curvature in the rounded surface of the R-section 4, it is necessary to detect and control the angle $\beta$ shown in FIG. 1, amount of movement in the direction W and the amount of movement in the direction V. An example of such a detection and control will be explained hereinunder with specific reference to FIGS. 7 and 8. Referring to FIG. 7, the angle $\beta$ is detected by a potentiometer 37 which is secured to a portion of the frame 30 and connected to a driving motor 34 for a segment gear 36, and which directly counts the number of rotation of the shaft of the motor 34. FIG. 8 shows the construction of the circumferential driving motor 24 and the axial driving motor 25, as well as the portion of the flaw detector around these motors. A potentiometer 38 is connected to the axial driving motor 25 to detect the amount of movement in the direction W by counting the number of rotations of the shaft of the motor 25. On the other hand, a rotary encoder 39 is connected to the circumferential driving motor 24 and detects the amount of movement in the direction V as the number of rotations of the shaft thereof. The control unit 40 performs a control in accordance with the thus detected angle $\beta$, the amount of movement in the direction W and the amount of movement in the direction V, such that the pivot axis of the probe 18 coincides with the center of curvature in the rounded surface of the R-section 4.

In the described embodiment, the amount of movement in the direction W is determined by the profiling signal produced by the position detector 20. This, however, is not exclusive and the amount of movement of the probe 18 in the direction W may be determined by a position detector which copies a model of the nozzle of the same size as the actual nozzle under examination and placed in the remote control room. As a modification, the model of the nozzle is formed to have a size greater than that of the actual nozzle, and the output from the position sensor copying the model is reduced by a ratio equal to the ratio of size between the actual nozzle and the model, so that the amount of movement of the probe is decreased by the above-mentioned ratio. Alternatively, the actual size of the nozzle is numeralized as values in three-dimensional coordinates and are inputted to a numerical controller as an operation command thereby to determine the amount of movement of the probe 18 in the direction W. Namely, it is possible to adopt a numerical control in place of the profile control. In such a case, however, there is a possibility that an error from the actual nozzle may be caused when the control is made by means of the operation command solely. To eliminate such an error, it is advisable to make use of a position detecting sensor 20 as in the case of the described embodiment. Namely, the error can be eliminated by detecting the error at each of a plurality of points previously determined in the direction V and effecting a suitable correction by a servo mechanism to negate such an error.

As has been described, according to the invention, the probe is supported pivotally around a pivot axis presented by a pivot shaft on the driving unit, and the control is made such that the pivot axis follows up the center of the arcuate surface of the outer peripheral corner section of the nozzle. It is, therefore, possible to achieve a full automatic and remote operation of the flaw detector except the attaching and detaching of the flaw detector and, hence, to achieve a higher degree of precision of flaw detection while reducing the number of inspectors working for the flaw detection.

In the flaw detector of the invention having the features stated above, once the driving unit constituted by the driving mechanism 16, the guide rod 29 and the frame 30 is set, it suffices only to rotatingly move the driving unit along the outer periphery of the nozzle body 2 while maintaining a predetermined angle to the nozzle body 2 and to move the same in the direction of axis of the nozzle (direction W). By so doing, the probe 18 pivots with the pivot axis coinciding with the center of curvature in the rounded surface of the R-section 4. Therefore, the direction of the flaw detection made by the probe 18 is changed regularly to facilitate the processing of the signals advantageously.

What is claimed is:

1. An ultrasonic flaw detector for detecting any flaw existing in the inner peripheral corner section of a joint portion between a cylindrical vessel and a cylindrical member projecting from the barrel of said cylindrical vessel by means of an ultrasonic wave applied from the outer peripheral corner section of said joint portion, said outer peripheral corner section having a rounded surface, said ultrasonic flaw detector comprising:

means for supporting a probe of said flaw detector such that said probe can pivot around an axis which coincides with the center of curvature of the rounded surface of said outer peripheral corner section of said cylindrical member; and means connectable to said supporting means for permitting said probe to move along the rounded surface of said outer peripheral corner section while traveling in a path peripherally around said cylindrical member and while making the pivot axis of said probe follow the locus of the center of curvature of the rounded surface of said outer peripheral corner section.

2. The ultrasonic flaw detector of claim 1, wherein said permitting means includes means for driving said supporting means axially along said cylindrical member.

3. The ultrasonic flaw detector of claim 1, wherein said permitting means carries said support means circumferentially around said cylindrical member.

4. The ultrasonic flaw detector of claim 3, wherein said permitting means includes means for driving said support means axially along said cylindrical member.

5. An ultrasonic flaw detector for detecting any flaw existing in the inner peripheral corner section of a joint portion between a cylindrical vessel and a cylindrical member projecting from the barrel of said cylindrical vessel by means of an ultrasonic wave applied from the outer peripheral corner of said joint portion, said outer peripheral corner section having a rounded surface, comprising:

a cylindrical track adapted to be secured around the outer periphery of said cylindrical member;

a driving mechanism mounted on said track and moveable along said track, said driving mechanism including a circumferential driving source and an axial driving source;

a rod slidably movable in the axial direction by said axial driving source of said driving mechanism;

a frame connected to said rod in such a manner as to be able to move in the radial direction of said cylindrical member;

a probe pivotally supported by said frame; and control means for controlling the movement of said probe such that the pivot axis of said probe follows the locus of the center of curvature of the rounded surface of said outer peripheral corner section of said joint portion.

6. An ultrasonic flaw detector as claimed in claim 5, wherein said control means includes:

(a) means for detecting the angle of pivotal movement of said probe;

(b) means for detecting the amount of movement of said probe in the axial direction;

(c) means for detecting the amount of movement of said probe in the circumferential direction; and (d) a unit for controlling said driving mechanism in accordance with the signals derived from the detecting means.

7. An ultrasonic flaw detector as claimed in claim 5, wherein said probe is driven by the driving sources secured to said frame and rotatively driven by a segment gear which rotates around the axis of rotation of said probe.

8. An ultrasonic flaw detector as claimed in claim 5, wherein said rod and said frame are moved along the outer periphery of said cylindrical member while maintaining a predetermined inclination angle to said cylindrical member.

9. The ultrasonic flaw detector of claim 5, wherein said control means includes first detector means mounted on said probe, for detecting and providing to said control means a first signal indicative of the axial position of said probe.

10. The ultrasonic flaw detector of claim 9, wherein said axial driving source is coupled to said control means and is adapted to be driven in response to said first signal.

11. The ultrasonic flaw detector of claim 10, wherein said control means includes second detector means connected to said axial driving motor, for detecting and providing to said control means a second signal indicative of movement of said probe axially along said cylindrical member.

12. The ultrasonic flaw detector of claim 11, wherein said control means includes third detector means connected to said cylindrical driving source, for detecting and providing to said control means a third signal indicative of movement of said driving mechanism along said track.

13. The ultrasonic flaw detector of claim 12, wherein said frame includes a rotational driving source operationally interconnected to said control means for pivoting said probe about said pivot axis.

14. The ultrasonic flaw detector of claim 13, wherein said control means includes fourth detector means for detecting and providing to said control means a fourth signal indicative of the directional angle of said probe.

15. An ultrasonic flaw detector for detecting any flaw existing in the inner peripheral corner section of a joint portion between a cylindrical vessel and a cylindrical member projecting from the barrel of said cylindrical vessel by means of an ultrasonic wave applied from the outer peripheral corner section of said joint portion, said outer peripheral corner section having a rounded surface, comprising:

a cylindrical track secured to the outer periphery of said cylindrical member;

a driving mechanism mounted on said track for movement along said track, said driving mechanism having a circumferential driving source and an axial driving source;

a rod slidably movable in the axial direction by said axial driving source of said driving mechanism;

a frame connected to said rod so as to be able to move in the radial direction of said cylindrical member;

a probe pivotally supported by said frame;

a position detecting means mounted on said frame and adapted to detect the axial position of said probe; and control means adapted for controlling said driving mechanism in accordance with a signal from said position detecting means such that the pivot axis of said probe follows the locus of the center of curvature of the rounded surface of said outer peripheral corner section of said joint portion.

* * * * *